United States Patent [19]
Venaille et al.

[11] Patent Number: 5,459,330
[45] Date of Patent: Oct. 17, 1995

[54] PROCESS AND DEVICE FOR THE INSPECTION OF GLASS

[75] Inventors: Christophe Venaille, Thorigne Fouillard; Denis Mischler, Acigne; Philippe Le Roy, Betton, all of France

[73] Assignee: Thomson-CSF, Paris, France

[21] Appl. No.: 196,212

[22] PCT Filed: Sep. 14, 1992

[86] PCT No.: PCT/FR92/00859

§ 371 Date: Mar. 14, 1994

§ 102(e) Date: Mar. 14, 1994

[87] PCT Pub. No.: WO93/06467

PCT Pub. Date: Apr. 1, 1993

[30] Foreign Application Priority Data

Sep. 13, 1991 [FR] France .................................. 91 11315

[51] Int. Cl.⁶ .................................................. G01N 21/89
[52] U.S. Cl. .................. 250/559.45; 250/559.48; 356/239; 356/430
[58] Field of Search ................... 250/562, 563, 250/571, 572, 234, 235, 223 B; 356/239, 240, 237, 430, 431

[56] References Cited

U.S. PATENT DOCUMENTS

| | | | |
|---|---|---|---|
| 3,652,863 | 3/1972 | Gaskell et al. | 356/239 |
| 4,182,575 | 1/1980 | Clark et al. | 356/239 |
| 4,568,984 | 2/1986 | Juergensen et al. | 250/572 |
| 4,597,665 | 7/1986 | Galbraith et al. | 250/572 |
| 4,697,082 | 9/1987 | Bartelsen | 356/239 |

*Primary Examiner*—Edward R. Westin
*Assistant Examiner*—John R. Lee
*Attorney, Agent, or Firm*—Oblon, Spivak, McClelland, Maier, & Neustadt

[57] ABSTRACT

A process and a device for inspecting glass including the use of a laser to illuminate successive cross section planes YX of a piece of glass to be inspected by relative displacement of a light curtain formed by the illumination source. A camera detects a reflective radiation emerging from the piece of glass in an observation direction which is oblique to the plane YZ of the light curtain in order to form images on the camera which include two lines corresponding to the upper and lower faces of the piece of glass and any possible luminous points situated between these two lines which would correspond to inclusions within the thickness of the glass.

7 Claims, 2 Drawing Sheets

PROCESS AND DEVICE FOR THE INSPECTION OF GLASS

BACKGROUND OF THE INVENTION

1. Field of the Invention

Process and device for the inspection of glass

The invention relates to the field of automatic industrial inspection and more particularly concerns a process, and the corresponding device, for the inspection of glass.

2. Discussion of Background

In a general way, the purpose of the inspection of glass is the detection and the locating of defects, called "inclusions", which are generated in the course of the manufacturing phase in pieces of glass. The effect of these defects on the quality of the glass produced depends on their number, their shape and the standards imposed on the glassmakers according to the application aimed at. These defects are of two types:

"seed" type: the defects are gas bubbles which have remained captive within the material in the molten state;

"stone" type: the defects are defects of homogeneity of the basic constituents involving the formation of a particle visible within the glass.

The size of these inclusions is in general less than 1 millimeter and the measuring thereof must be carried out with a high precision, at least for certain applications, the precision required possibly ranging from $1/10$ to $1/100$ of a millimeter.

The automatic detection of these defects is of great importance to glassmakers: a solution to this problem permits both an enhancement of the quality of the glass manufactured (improved compliance with the quality standards) and the availability of reliable statistics on the number and the size of the defects in order to modify, in consequence, the various production parameters of the glass.

The processes of inspection of glass which are currently known are restricted to the visual examination of the glass by a human observer. In fact, attempts to use artificial vision for the inspection of glass have not, up to the present time, given any results since these solutions effect a two-dimensional processing of the information. Accordingly, the corresponding processes do not permit the effective discrimination of the surface defects, dust and scratches, etc. . . . , which are eliminated by a single polishing of the glass, from the inclusions which are concealed in the mass of the glass.

SUMMARY OF THE INVENTION

The subject of the invention is a process for the inspection of glass, and the corresponding device, which permits the avoidance of the disadvantages of the conventional methods by permitting both the locating of the defects at the surface as within the thickness of the glass and an approximate knowledge of their positions within the thickness of the glass; this permits a very good discrimination between surface defects and inclusions.

According to the invention, the inspection process utilizes a three-dimensional processing and for that purpose effects a localized illumination of the glass by a laser beam, and an adapted detection which permits the separate viewing of the upper face of the glass and its lower face and, between the two, its thickness.

According to the invention, a process for the inspection of a glass by illumination by means of a light source external to the illumination surface, characterized in that it consists in illuminating the illumination surface by a laser beam applied in a direction almost perpendicular to the illumination face to form a light curtain in the form of a plane traversing the glass in its thickness, in order to detect by a camera the reflected radiation emerging from the piece of glass in an observation direction which is oblique in relation to the direction of the plane formed by the light curtain when inclusions are present in the glass at the location of the light curtain, and to view, via the camera, the image of the inclusions which is thus obtained, between two lines representing respectively the light beams slightly reflected by the entrance surface and the exit surface of the light beam in the course of its passage within the thickness of the glass.

The subject of the invention is also the inspection device intended to carry out the process as described hereinabove.

BRIEF DESCRIPTION OF DRAWINGS

The invention will be better understood and further features will become evident with the aid of the description which follows, with reference to the accompanying figures.

DETAILED DESCRIPTION OF THE PREFERRED EMBODIMENTS

Figure 1:
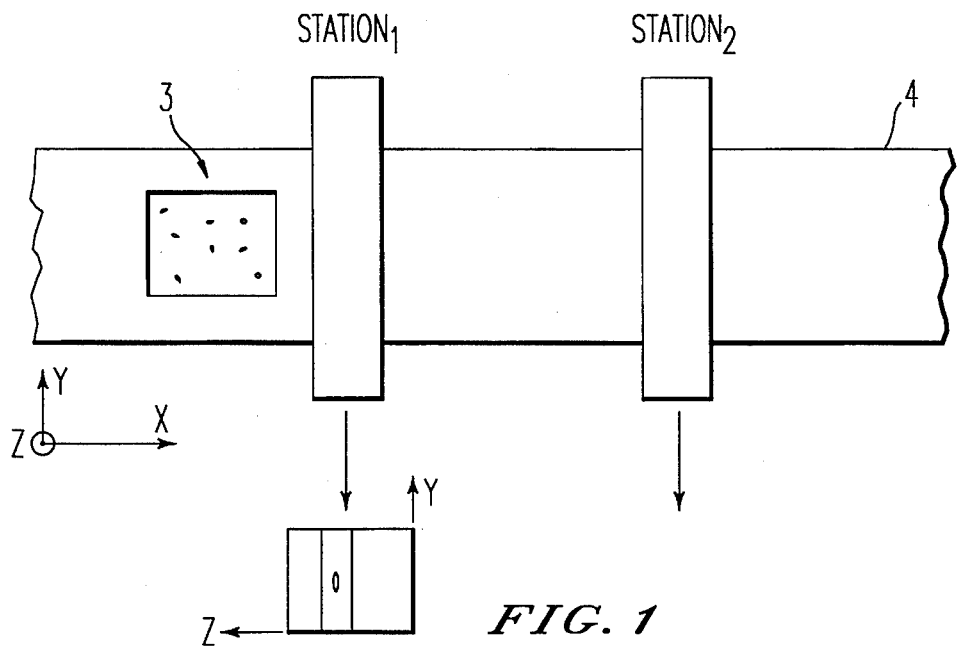
FIG. 1 is a diagram of the inspection device according to the invention.

The device for the inspection of glass according to the invention includes, in an embodiment diagrammatically illustrated in top view in FIG. 1, two stations, a station 1 for the detection and locating of the defects in three dimensions, X, Y, Z and a station 2 for classification and measurement of these defects. The piece of glass 3 is placed on a conveyor 4 and analysed progressively as it passes vertically under the station 1 for the detection and the locating of the defects, the displacement of the conveyor taking place along the axis X. The station 1 provides an image of the successive sections of the piece of glass (in the plane YZ), such as that shown in FIG. 1, where an inclusion has been represented between two lines corresponding respectively to the upper surface and to the lower surface of the glass.

Figure 2:
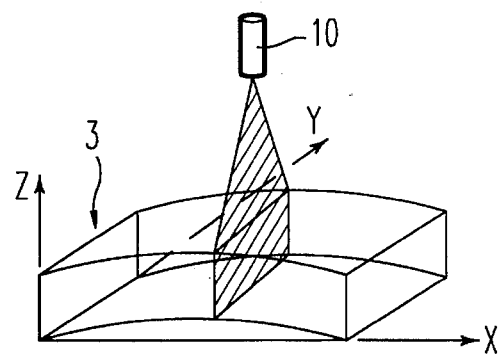
FIG. 2 is a detailed diagram of the device.

To do this, the first station is constituted in the following manner. It includes an illumination source 10 of heliumneon, HeNe laser type, illustrated by FIG. 2. The beam emitted by the laser source is broadened by an optical rod disposed at the exit of this source in such a manner as to constitute a type of light curtain, of adapted thickness, as illustrated in FIG. 2, which corresponds at each instant to a section YZ of the piece of glass. This light curtain accordingly illuminates the glass perpendicularly to the plane of the conveyor and thus successively encounters:

the upper face of the piece of glass, possibly, the inclusions to be detected, the lower face of the piece of glass.

Figure 3:
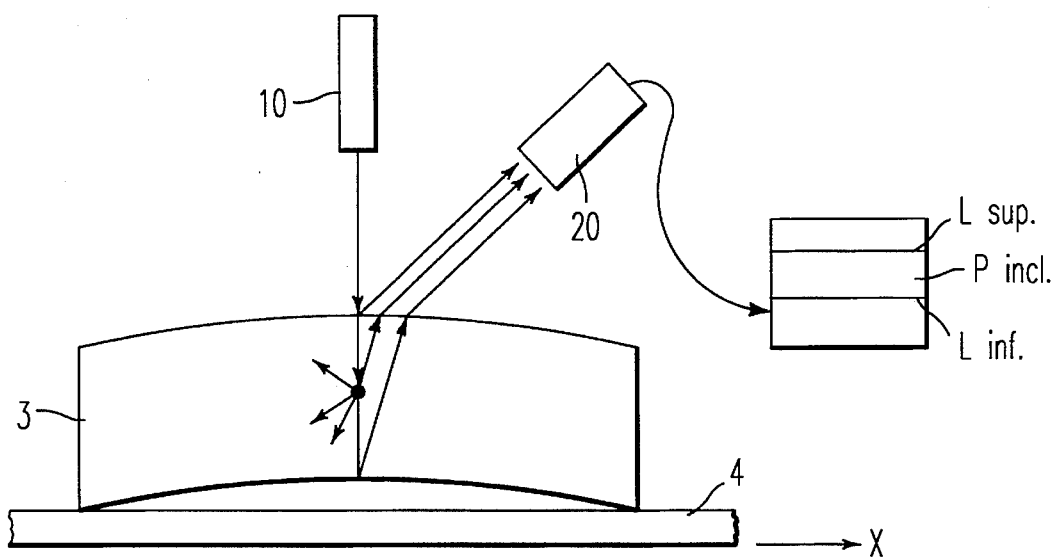
FIG. 3 illustrates the principle of the illumination of the glass according to the invention.

A camera 20 placed above the glass and obliquely in relation to the light curtain, as illustrated in section by FIG. 3, is intended to sense the radiation emerging from the piece of glass in its direction, referred to as the observation direction, and thus sees these interruptions respectively as:

a line Lsup corresponding to the upper face possibly, a highly luminous point Pincl in the event of inclusion;

a line Linf corresponding to the lower face.

The corresponding lines may be strokes if the intersection of the light curtain and of the upper face of the glass is a straight line, or curved lines for a spherical or cylindrical face if the curvature extends in the direction of the light curtain.

Figure 4D:
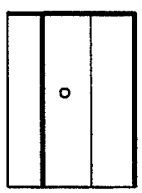
FIGS. 4A, 4B, 4C and 4D are explanatory diagrams.
Figure 4C:
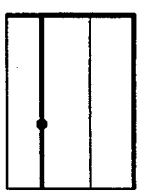
Figure 4B:
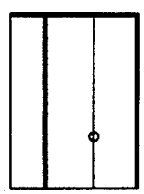
Figure 4A:
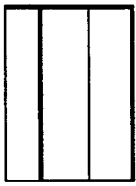

In this configuration, the defects appear in the following manner:

an inclusion produces a luminous point situated in the image between the two lines due to the upper and lower faces, as illustrated in FIG. 4a;

a surface defect produces a luminous point which is partially coincident with the line of the upper face, as illustrated by FIG. 4b;

a defect on the surface of the base produces a luminous point which is partially coincident with the line of the lower face, as illustrated by FIG. 4c;

finally, if there is no defect, only the two strokes corresponding to the upper and lower faces appear in the image, as illustrated by FIG. 4d.

In accordance with this principle, the process of inspection of a piece of glass, consists in causing this piece of glass to pass on the belt of the conveyor 4 under the station 1 including the laser source and the camera system, the belt being driven with a uniform translational movement. To cover the width of the piece inspected, the laser beam is selected to be sufficiently spread out; if the width of the piece exceeds the possible expansion width of the beam, the optical laser illumination device will be reproduced as many times as necessary. Likewise, if the field of the camera is not sufficiently broad, the station 1 is equipped with additional cameras to cover the useful field.

The images are acquired by the system of cameras at video frequency; the sequence of images which is thus obtained forms the subject of a processing within a data processing device which permits the detection and the monitoring of the two lines associated with the surfaces as well as one or more inclusions between these two lines. The information supplied by the station 1 is accordingly a location by imaging of the defects in three dimensions X, Y and Z.

The information on the luminance of the defect further permits the approximate quantification of the size of the defects, and this information can be exploited by the station 2 for classification and measurement.

In an embodiment of the inspection device, the features of the illumination system are such that the source is a heliumneon laser source as indicated hereinabove, the means for expansion of the beam emanating from the laser source are constituted by an optical rod or by a plane or concave semicylindrical diverging lens, in such a manner as to spread the laser beam in a single direction; the thickness of the laser curtain must be greater than the size of the defects in such a manner as to guarantee the detection of the defect in all cases.

As regards the imaging system, the sensors employed are of the CCD type; the number of sensors is dependent upon the width of the piece of glass to be inspected and upon the desired resolution.

Figure 5:
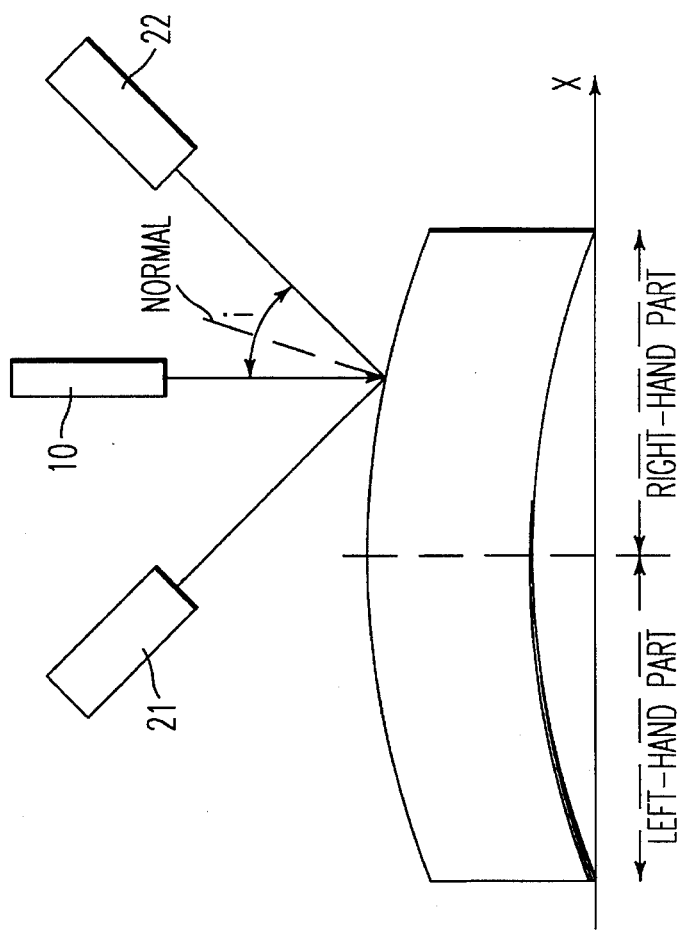
FIG. 5 is an optical diagram.

Furthermore, in one embodiment, in the case of convex curved surfaces, as illustrated by FIG. 5, the number of cameras is doubled so as to avoid parasitic phenomena due to multiple reflections of the laser beam in the glass, which might generate in the image luminous lines of lesser energy within the above-described two lines. In a more general way, the doubling of the processing of the information permits the device to be made more robust, especially in the case of a dusty atmosphere. In this case, two cameras are placed symmetrically in relation to the laser, the axis of which is vertical. The angle of incidence (i) between the laser and the optical axis of the camera is selected in such a manner that one of the axes of the two cameras is always situated on the opposite side to the laser beam in relation to the normal to the surface of the glass. Thus, for the left-hand part of the piece the camera 21 will be used, while for the right-hand part of the piece the camera 22 will be used.

As regards the optical system of the camera, at the location of the station 1 the problem is not precision but simply the detection and the localization of the defects, the coordinates of which along the axes X, Y and Z are then communicated to the station 2 for precise measurement. The optical system of the camera is thus selected in the following manner.

For the magnification, a compromise is achieved between a great depth of field which permits the clear observation of the entire thickness of the glass (low magnification) and a greater magnification which itself has the benefit of being able to separate the inclusions from the two surface strokes.

Furthermore, the optical system of the camera includes an anamorphoser: in practice, it is not necessary to have the same resolution along the two axes of the image. A good precision is required along the vertical axis in such a manner as to separate correctly the inclusions from the two surface lines (which are the two horizontal lines on the images of FIGS. 4a to 4d; on the other hand, it is desired to be able to cover the widest possible band of glass along the horizontal axis (Y) in such a manner as to limit the number of cameras necessary and the power of the data processing. For this reason, an anamorphotic optical system is used to ensure an anisotropic magnification in the image along the two orthogonal directions X and Z.

The analysis of the images thus obtained in the course of the passing of the piece of glass carried by the conveyor vertically under the observation station permits the extraction of the useful information and especially:

the luminance;

the position of the inclusions, that is to say the coordinates (u,v) of the points appearing with excess brightness in the image;

the movement of these points on a sequence of two or three consecutive images;

the size of these points.

The processing of this information and of the information known a priori as to the shape and the dimensions of the piece inspected permit an automatic processing.

The invention is not limited to the process and to the device for the inspection of glass as described in detail hereinabove. In particular, there has been described a conveyor on which there is entrained a piece of glass which passes vertically under an observation station. However, it is possible to use, without departing from the scope of the invention, a movable observation station, the material to be inspected remaining fixed. This arrangement is in particular beneficial for large pieces of glass to be inspected.

Furthermore, the camera has been provided in the example to form an image from the radiation emerging in the observation direction. In order to improve the image obtained on the detector of the camera, it is possible to introduce into the path of the detected radiation an optical system which would facilitate the formation of the useful image, especially an optical filter transmitting to the detector the radiation emerging at the wavelength of the laser source used.

We claim:

1. A process for inspecting glass comprising the steps of:

illuminating by means of a light source, a surface of said glass wherein said light source is a laser beam applied in a direction substantially perpendicular to a surface of said glass to form a light curtain in the form of a plane YZ transversing said glass within its thickness;

detecting by means of a camera, reflected radiation emerging from said glass in an observation direction which is oblique in relation to the direction of said plane YZ formed by said light curtain wherein said reflected radiation provides images of two lines representing said illuminated surface and an exit surface of the light beam during its passage within the thickness of the glass, said emerging radiation also providing to said camera an image of inclusions in said glass and wherein the position of said image of said inclusions with respect to said two lines determines the location depth of said inclusions within a thickness of said glass.

2. The process according to claim 1 wherein said glass is placed on a conveyor which passes in a horizontal plane XY at right angles to said laser light curtain YZ created by a fixed observation station, said image being taken by said camera which is likewise fixed and the axis of said camera being oblique in relation to said light curtain.

3. The process according to any one of claims 1 or 2 wherein said radiation emerging from said piece of glass is detected in an oblique direction whereby an axis of said laser source and an observation axis are situated on either side of a perpendicular to the surface of said glass in order to avoid parasitic reflections occurring before said step of detection.

4. A device for inspecting glass, comprising:

an observation station including an illumination laser source coupled to a means for expansion of a beam of said laser source in a single direction Y to thereby form a light curtain in a plane YZ which plane is orthognal to a support plane XY for said glass to be inspected;

a camera having an axis oblique in relation to said plane of said light curtain wherein said camera senses radiation from said laser source and reflected by said glass, whereby said reflected radiation includes an image having a first second line representing respectively reflections from a top surface and a bottom surface of said glass and an image of inclusions fixed between said two lines providing an indication of a defect in said glass and the location of said defect within the thickness of said glass as a function of the distance between said inclusion image and said two lines.

5. Device according to claim 4 further including a second camera whereby said camera and said second camera are respectively situated on each side of said illumination source in relation to said plane of said light curtain in order to provide for inspection of non-plane glass.

6. The device according to any one of claims 4 or 5 further including at least one second illumination source for inspecting glass having a large width greater than said light curtain wherein each of said at least one second light source forms a respective light curtain wherein the set of light curtains including said light curtain and said respective light curtains create a complete cross-sectional plane of said glass.

7. The device according to any one of claims 4 or 5 further including an anamorphotic optical device associated with said camera to permit an observation of a plane of said glass over a width along the direction Y, without affecting observation of thickness along direction Z.

* * * * *